United States Patent

Zobac et al.

[11] 4,345,598
[45] Aug. 24, 1982

[54] CRYOGENIC APPARATUS FOR SURGERY

[75] Inventors: Ladislav Zobac, Brno; Zdenek Malek, Prague; Frantisek Soukup, Roztoky U Praha; Antonin Ryska, Prague; Jan Jelinek, Prague; Jiri Busta, Prague, all of Czechoslovakia

[73] Assignee: Vyzkumny ustav Silnoproude Elektrotechniky, Prague, Czechoslovakia

[21] Appl. No.: 134,415

[22] Filed: Mar. 27, 1980

[51] Int. Cl.³ .............................................. A61B 17/36
[52] U.S. Cl. ................................... 128/303.1; 128/399
[58] Field of Search ..................... 128/303.1, 399, 400, 128/401, 402, DIG. 27; 62/514 JT, 293

[56] References Cited

U.S. PATENT DOCUMENTS

| | | | |
|---|---|---|---|
| 2,645,095 | 7/1953 | Posch | 128/303.1 |
| 3,537,458 | 11/1970 | Lange | 128/303.1 |
| 3,807,403 | 4/1974 | Stumpf et al. | 128/303.1 |
| 3,948,269 | 4/1976 | Zimmer | 128/303.1 |
| 3,971,383 | 7/1976 | Van Gerven | 128/303.1 |
| 4,211,231 | 7/1980 | Rzasa | 128/303.1 |

FOREIGN PATENT DOCUMENTS

| | | | |
|---|---|---|---|
| 2834741 | 3/1979 | Fed. Rep. of Germany | 128/303.1 |
| 1342348 | 1/1974 | United Kingdom | 128/303.1 |
| 474341 | 6/1975 | U.S.S.R. | 128/303.1 |
| 482167 | 8/1975 | U.S.S.R. | 128/303.1 |
| 610524 | 6/1978 | U.S.S.R. | 128/303.1 |
| 532975 | 11/1978 | U.S.S.R. | 128/303.1 |

Primary Examiner—Stephen C. Pellegrino
Assistant Examiner—Daniel P. Burke

[57] ABSTRACT

Cryogenic apparatus for surgery operating with liquid cryogenic medium in a closed circuit, provided with an applicator and porous heat exchanger particularly adapted for tumor surgery, operating at an overpressure of the order of 10 kPa, with the possibility of adjustment of the cooling effect, quick response and possibility of selection of the position of the surgical instrument.

3 Claims, 1 Drawing Figure

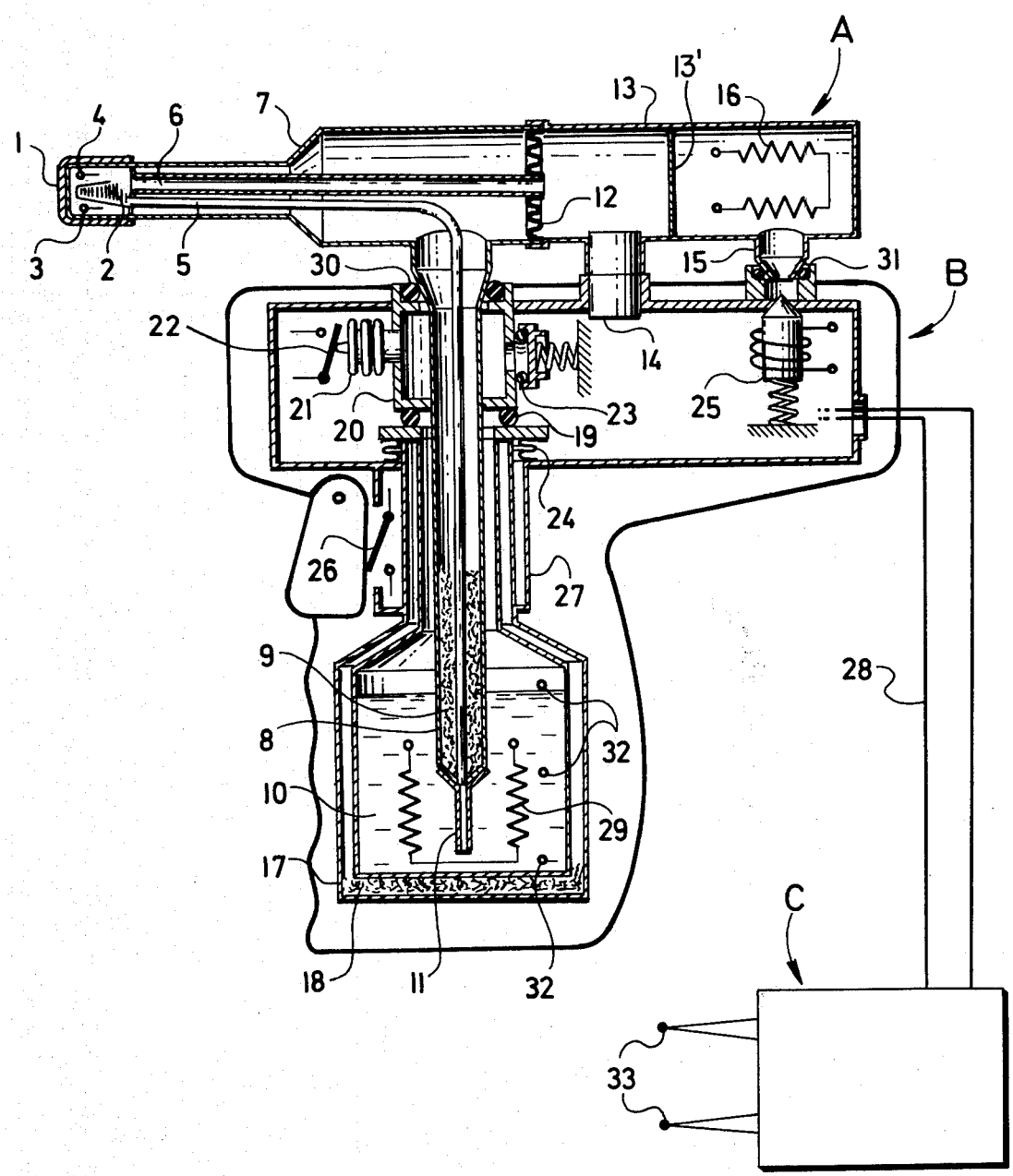

CRYOGENIC APPARATUS FOR SURGERY

BACKGROUND OF THE INVENTION

The invention relates to cryogenic apparatus for surgery with a closed cooling circuit comprising a holder of the surgical instrument provided with an applicator with a porous heat exchanger composed of metal grids or of sintered metal, advantageously of silver or copper, a storage vessel for liquid gas in a handle and a regulating unit.

Cryogenic surgical systems, frequently also called cryocauters, have been recently more widely used in surgery of tumorous diseases, where for cooling of a warm instrument applied to the place to be surgically treated either the expansion of some compressed gases, for instance carbon dioxide $CO_2$ or nitrogen oxide $N_2O$ or on internal circulation of liquefied gases, mostly nitrogen are used.

Systems with expansion cooling operate usually with an overpressure about 5 MPa, which must be also present in the surgical instrument itself which is relatively dangerous. Systems with cooling by a cyrogenic liquid are usually designed to operate either by gravity, where the liquid nitrogen flows from a storage vessel of the cryocauter, where it has been prior poured in an estimated amount through an insulated tube to the surgical instrument which it cools and is discharged in gaseous condition through another tube, or they operate at a pressure about 0.5 MPa, where liquid medium is supplied from an external storage vessel to the surgical instrument, where it turns into gas and is removed through a system of connecting tubes back to the storage vessel, where it is discharged into the atmosphere.

Systems operating by gravity have serious drawbacks in a very slow cooling and the impossibility of adjustment of the extent of cooling otherwise than by the variation of the amount of the cooling liquid filled into the storage vessel. Another limitation is the necessity to maintain a predetermined position of the surgical instrument in order to prevent spilling of the cryogenic liquid but of the storage vessel in the course of the surgical treatment.

Pressure systems provided with an external storage vessel for the cryogenic liquid enable dosing of the cooling effect and in some cases also the adjustment of the temperature, but they involve the risk connected with the high overpressure of about 0.5 MPa in the thin-walled surgical instrument. In addition the long connecting supply tube for liquid nitrogen is at the start of the surgery cooled for a relatively long time, the cooling of the instrument in contact with the tissue to a temperature below $-150°$ C. lasts even several minutes; this leads in case of surgery of tumorous diseases to a low efficiency of necrotization of tumorous cells.

SUMMARY OF THE INVENTION

It is an object of this invention to eliminate or at least substantially reduce these drawbacks and to provide a cryogenic apparatus capable to operate quickly, with a small overpressure of the cryogenic liquid and capable of adjustment of the cooling effect, of a quick cooling and with the possibility of selection of the position of the surgical instrument.

The apparatus, according to this invention, comprises a holder of the surgical instrument, provided on one side with an applicator, in the hollow space of which a porous heat exchanger and electrical heating elements are provided, on the other side with a heating device of gases passing from the applicator. The holder is exchangeably connected mechanically and electrically with a handle, in the lower part of which a storage vessel of liquid gas is arranged and which is provided with heating means with a safety pick-up device and level indicators. A pressurizing switch with a pressure indicator and an electromagnetic regulating valve seated gas tightly on an outlet extension of the holder, controlled by a change-over switch are provided in the handle. The handle is electrically connected with an indicating and regulating or controlling unit.

DESCRIPTION OF THE DRAWING

An exemplary embodiment of a cryogenic surgical apparatus according to this invention is diagrammatically indicated in the attached drawing; in which the single FIGURE is a view partially in side elevation and partially in vertical section through a preferred embodiment of the apparatus.

A holder A of a surgical instrument, which is exchangeable, comprises an applicator 1 containing a porous heat exchanger 2 with electrical heating elements 3 and a thermometer 4. The external diameter of the applicator 1 used is generally equal to the external diameter of a tube connecting the applicator 1 with a heat non-conducting mantle 7 of the exchangeable holder A of the surgical instrument; it can be, however, larger or smaller. A not shown surgical end piece can be fixed to the applicator 1. The input side of the porous heat exchanger 2 is connected to a supply tube 5 of liquefied nitrogen 10, the output side to a discharge tube 6, over which nitrogen is removed and through which conduits to heating elements 3 and to the thermometer 4 pass. The vacuum mantle 7 is exhausted to a pressure below $10^{-2}$ Pa. The supply tube 5 is bent and passes through a vertical extension 8 of the vacuum mantle 7 to a storage vessel 17 of liquid nitrogen 10, situated, as will be explained later, in the T-shaped mounting part B of the shape having a head and a stem in the a handle. The space between the vertical extension 8 of the vacuum mantle 7 and the supply tube 5 is filled by an absorbent 9, for instance with active carbon. An inlet extension 11 enabling a step-by-step adjustment of the upper level of the cooling effect, for instance extensions with different diameters of the input capillary or possibly a liquid and gas tight closure of the supply tube 5 are connected removably to the lower end of the vertical extension 8 of the vacuum mantle 7. The discharge tube 6 is connected with the vacuum mantle 7 of the exchangeable holder A of the surgical instrument vacuum tightly by a resilient element 12, for instance by a diaphragm. A sleeve 13 with an electric connector 14, an electric heating element 16 and an outlet extension 15 are gas tightly connected around the rim of the diaphram 12 with the vacuum mantle 7 of the exchangeable holder A. Thus gas flowing through the discharge tube 6 flows within sleeve 13 past a gas-permeable reinforcing member 13' into contact with heating element 16 and out through outlet extension 15.

The porous heat exchanger 2 comprises for instance a column of parallel plane metal grids, oriented perpendicularly to the axis of the applicator 1. The mutual relation of the diameter of the grid wires and of the size of openings of the grid is best close to one. The heat exchanger 2 can be however also made of sintered metal with high heat conductivity in the region of low temperature, such as silver or copper.

The stem or handle B comprises a chamber 20 which is over a packing 19 connected to a storage vessel 17, in the vacuum mantle of which an adsorbent 18, a pressure indicator 21 with a pressurizing switch 22, a safety valve 23, a spring 24, an electromagnetic regulating valve 25, a counter-piece of the electric connector 14 and a manually controlled change-over switch 26 of functions in the holder 27 are provided. There are furthermore in the handle part of member B an electric heating element 29 with a protective pick-up device and resistance level indicators 32 in the storage vessel 17.

The exchangeable holder A of the surgical instrument is adapted for connection with the head part of the T-shaped member B, on which it is shifted down whereby the vertical extension 8 of the vacuum mantle 7 of the holder A is dipped into the liquid nitrogen 10 and closes by the inlet packing 30 gas tightly the space above the level of the liquid nitrogen 10 in the storage vessel 17. Simultaneously, the sleeve 13 of the exchangeable holder A is connected by means of the outlet extension 15 over the outlet packing 31 gas tightly to the electromagnetic regulating valve 25. In addition, both parts of the electric connector 14 come into engagement, connecting the exchangeable holder A of the surgical instrument to the handle B. The connection with the indicating and regulating or controlling unit C is secured by a system of conductors 28. The electrical indicating and regulating or controlling unit C is provided with a pick-up device 33 of the temperature of the tissue.

The exchangeable holder A of the surgical instrument can be removed from the B and can be sterilized. Just prior to finished sterilization, liquid nitrogen 10 is filled into the storage vessel 17 over an opening in the inlet packing 30 of the vertical extension 8. The level of the liquid nitrogen 10 is indicated by resistance level indicators 32. The sterilized exchangeable holder A of the surgical instrument is plugged in into the head of the member B so, that is connects both parts of the electric connector 14 and the inlet packing 30 and the outlet packing 31 are gas tightly closing the vertical extension 8 of the mantle 7 with the handle part of member B.

By immersion of the vertical extension 8 into the liquid nitrogen 10 the absorbent 9 is cooled down, improving thereby the vacuum in the mantle of the storage vessel 17 and thus also the heat insulation of the supply tube 5 and of the discharge tube 6. Due to spontaneous evaporation of liquid nitrogen 10 from the storage vessel 17, pressure is increasing in the space above the level. The cut-in electrical indicating and regulating or controlling unit C feeds the electric heating element 29 with the safety pick-up device, thus speeding-up the pressure increase. Due to pressure increase, the length of the pressure indicator 21 is increased up to a position where the pressurizing switch 22 cuts out current from the source of the electrical indicating and regulating or controlling unit C. So far the cooling of the instrument is not caused to act, the pressure above the level of the liquid nitrogen increases due to the spontaneous evaporation, however solely up to a value, for which the safety valve is adjusted. After this pressure is attained, this valve is opening and prevents any further pressure increase.

In case of a failure of the safety valve 23, the safety connection of the storage vessel 17 is operating secured by the spring 24 chosen so that the tightness of the connection is disturbed in case a certain pressure in the storage vessel 17 is surpassed.

When the electromagnetic regulating valve 25 is closed, the gas pressure on the outlet side increases with the gas pressure in the storage vessel 17, and the liquid nitrogen cannot be forced out of the storage vessel 17. A further safeguarding against unwelcome overpressure provides the electromagnetic regulating valve 25, the pressure spring of which is selected so as to open the valve spontaneously at an overpressure for 10 kPa higher than which the above mentioned safety valve 23 and the spring 24 are adjusted.

From the moment of connection of the electric indicating and regulating or controlling unit C the temperature of the applicator 1 is automatically adjusted by means of the electric thermometer 4 and of regulating circuits to the temperaure 37° C. of the human body by way of electric heating elements 3. The electric heating element 16 is in addition preheated to a temperature which is measured by a heat depending-resistance, which is in thermal contact with the electric heating element 16 in order to increase the initial temperature of the heating element 16 already prior to passage of the cold gas. This temperature is increased after closing the electromagnetic regulating valve 25.

By closing the change-over switch 26 in the holder 27, the electromagnetic valve 25 is opened by the voltage from the indicating and regulating unit C, whereby the circulation of the cooling medium is started and simultaneously the reference voltage corresponding to the temperature 37° C. is switched over to a prior selected low temperature and simultaneously the heating elements 3 are disconnected up to the moment where the electric thermometer 4 or the pick-up device of the temperature indicates that the preselected temperature has been established, whereby the values of both limit temperatures of both indicators may be different. This is particularly advantageous for the possibility of operation of the applicator 1 in the region of lowest obtainable temperature at a guaranteed safety of the surgery by checking the temperatures at the place of the tissue, where a certain limit of overcooling must be surpassed.

In the course of the process of cooling of the applicator 1, the pressure indicator 21 and the pressurizing switch 22 secure furthermore a two-stage regulation of pressure above the level of liquid nitrogen 10 by means of the electric heating device 29 with a protective pick-up device, indicating a possible exhaustion of liquid nitrogen 10, so that the heating device 29 cannot be destroyed even in case the attendant overlooks indications of the resistance level indicators 32. In addition, in case the cooling medium circulates, with change-over switch 26 in the closed position, the electric heating element 16 of the discharged nitrogen is adjusted to a higher value of working temperature than would correspond to the rest condition in order to secure the required heating of the discharged gas above 0° C.

The closing of the electromagnetic regulating valve 25 causes an instantaneous start of heating of the applicator 1 by the electric heating elements 3. After the temperature of 37° C. has been reached on the applicator 1, the holder A of the surgical instrument is taken off or removed from the tissue and if a sufficient amount of liquid nitrogen 10 is still in the storage vessel 17, which is indicated by the level indicators 32, the holder A of the instrument can be removed and replaced by another holder A of a surgical instrument, which has been in the meantime sterilized.

The shape of the holder A of the surgical instrument and of the handle part of member B can be altered so that the fundamental approach of the instrument to the treated tissue is horizontal, inclined or also vertical.

A laboratory trial apparatus according to this invention has been tested on egg white which has been thermostated to 37° C. and it has been repeatedly proved, that the time of undercooling of the applicator 1 without a shaped extension end piece to a temperature below −190° C. from the initial temperature 37° C. can be varied by the size of the removable inlet extension 11 according to need from 10 seconds on if a porous heat transmitter 2 is used. If an end piece is screwed onto the face part of the applicator 1, the cooling time is prolonged from 10 to 20 seconds according to the thermal capacity of the end piece. These results have been obtained at a working overpressure in the storage vessel 17 within the range between 10 to 25 kPa. The speed of growth of the diameter of the ice formation in the egg white was thereby from 0.1 to 0.3 mm per second. A verification made on livers of a live rabbit showed that even in a tissue filled with blood, the speed of growth of the diameter of the ice formation remains within the order of 0.1 mm per second.

An advantage of the apparatus according to this invention is above all its safety; as the apparatus operates with a small overpressure of the order of 10 kPa with independent safety means, the surgeon is not limited in his movements by connecting tubes and all required parameters can be adjusted on the handle part of member B and on the indicating and regulating or controlling unit C.

Although the invention is illustrated and described with reference to one preferred embodiment thereof, it is to be expressly understood that it is in no way limited to the disclosure of such a preferred embodiment, but is capable of numerous modifications within the scope of the appended claims.

We claim:

1. Cryogenic apparatus for surgery comprising a hand-held mobile surgical instrument, the surgical instrument comprising an elongated hollow holder, a hollow applicator on a first end of the holder, a porous heat exchanger and an electrical heating unit disposed within the applicator, a heating device for gases escaping from the applicator disposed near the second end of the holder, a mounting member for the holder, said mounting member generally of T-shape and having a head portion in the form of an elongated generally horizontal hollow part upon which the holder is mounted and a handle portion disposed generally vertically, means for exchangeably mechanically and electrically connecting the head of the mounting member to the holder, a storage vessel for liquefied gas disposed within the handle portion of the mounting member remote from the holder, conduit means leading from storage vessel in the handle portion of the mounting means to the applicator in the holder, and a pressurizing switch with a pressure indicator and an electro-magnetic regulating valve disposed within the mounting member, the holder having an extension remote from the applicator thereon, the electro-magnetic regulating valve being seated air tightly on said head portion of the mounting member, said porous heat exchanger being composed of a pile of metal grids situated in planes perpendicular to the axis of the applicator.

2. Cyrogenic apparatus for surgery as claimed in claim 1, comprising a change-over switch mounted on the handle portion of the mounting member, circuit means connecting said change-over switch to the electro-magnetic regulating valve for controlling it, an indicating and controlling unit for the surgical instrument disposed separate therefrom, and circuit means connecting the controlling unit to the surgical instrument.

3. Cryogenic apparatus for surgery as claimed in claim 2, wherein said controlling unit comprises a temperature sensor for the tissue being operated upon by the surgical instrument.

* * * * *